United States Patent
Hartman et al.

(10) Patent No.: US 9,421,200 B1
(45) Date of Patent: *Aug. 23, 2016

(54) TREATING PAIN IN PATIENTS WITH HEPATIC IMPAIRMENT

(71) Applicant: Pernix Ireland Pain Limited, Dublin (IE)

(72) Inventors: Andrew Hartman, Belmont, CA (US); Christopher M. Rubino, Williamsville, NY (US); Cynthia Y. Robinson, Burlingame, CA (US)

(73) Assignee: Pernix Ireland Pain Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/154,524

(22) Filed: May 13, 2016

Related U.S. Application Data

(63) Continuation of application No. 14/978,217, filed on Dec. 22, 2015, now Pat. No. 9,339,499, which is a
(Continued)

(51) Int. Cl.
  *A61K 9/16* (2006.01)
  *A61K 31/485* (2006.01)
  (Continued)

(52) U.S. Cl.
  CPC ........... *A61K 31/485* (2013.01); *A61K 9/0053* (2013.01); *A61K 9/4808* (2013.01); *A61K 9/5026* (2013.01)

(58) Field of Classification Search
  CPC .................................................. A61K 9/1676
  See application file for complete search history.

(56) References Cited

U.S. PATENT DOCUMENTS 5,478,577 A 12/1995 Sackler
6,066,339 A 5/2000 Stark
(Continued)

FOREIGN PATENT DOCUMENTS

| EP | 2311442 A1 | 4/2011 |
| WO | 02/092060 A1 | 11/2002 |
| WO | 2009/036287 A1 | 3/2009 |

OTHER PUBLICATIONS

Darwish, Mona et al., Dose Proportionality of a Hydrocodone Extended-Release Tablet Formulated with Abuse-Deterrence Technology, Original Research Article, Mar. 27, 2015, 7 pages.
(Continued)

*Primary Examiner* — Benjamin Packard
(74) *Attorney, Agent, or Firm* — Servilla Whitney LLC

(57) ABSTRACT

An extended release composition for an analgesic active pharmaceutical ingredient which may be an opioid, preferably hydrocodone as the only active ingredient. The extended release composition preferably comprises a extended release composition which may be in the form of beads contained in an oral dosage form such as gelatin capsules. The composition is designed to release hydrocodone in a way such that the increase in hydrocodone exposure in hepatically impaired patients is not clinically significant. The oral dosage units are supplied as part of a kit, which also includes a primary package and a package insert all sold as a commercially marketed product. The primary package and package insert are contained in an optional secondary package and the package insert does not contain a warning, a dosing instruction, or a dosing table specifically directed to patients suffering from mild, moderate or severe hepatic impairment, and preferably explicitly states that dosing adjustment is not required for mild or moderate hepatic impairment.

20 Claims, 7 Drawing Sheets

|  | Mild Impairment[1] | Moderate Impairment[2] | Severe Impairment[3] |
|---|---|---|---|
| HC-ER | | | |
| $C_{max}$ | 1.08 | 1.10 | ND[4] |
| $AUC_{0-inf}$ | 1.10 | 1.26 | ND |
| Oxycontin® (oxycodone hydrochloride extended release tablets)[5] | | | |
| $C_{max}$ | NR[6] | 1.5 | NR |
| AUC | NR | 1.95 | NR |
| Nucynta® ER (tapentadol extended oral-release tablets)[7] | | | |
| $C_{max}$ | 1.4 | 2.5 | NR |
| AUC | 1.7 | 4.2 | NR |
| Opana® ER (oxymorphone hydrochloride extended release tablets)[8] | | | |
| $C_{max}$ | NR | NR | NR |
| AUC | 1.6[9] | 3.7[9] | 12.2[9,10] |
| Exalgo® (hydromorphone hydrochloride extended release tablets)[11] | | | |
| $C_{max}$ | NR | ~4.0 | NR |
| AUC | NR | ~4.0 | NR |

Related U.S. Application Data continuation of application No. 14/815,219, filed on Jul. 31, 2015, now Pat. No. 9,265,760, which is a continuation of application No. 14/523,162, filed on Oct. 24, 2014, which is a continuation-in-part of application No. 13/950,969, filed on Jul. 25, 2013.

(60) Provisional application No. 61/677,601, filed on Jul. 31, 2012, provisional application No. 61/779,698, filed on Mar. 13, 2013.

(51) Int. Cl.
*A61K 9/00* (2006.01)
*A61K 9/48* (2006.01)
*A61K 9/50* (2006.01)

(56) References Cited

U.S. PATENT DOCUMENTS

| | | | |
|---|---|---|---|
| 7,790,215 | B2 | 9/2010 | Sackler |
| 8,647,667 | B2 | 2/2014 | Oshlack |
| 8,808,740 | B2 | 8/2014 | Huang |
| 8,969,369 | B2 | 3/2015 | Caruso |
| 2005/0232987 | A1 | 10/2005 | Srinivasan |
| 2006/0003004 | A1 | 1/2006 | Hirsh |
| 2006/0240105 | A1 | 10/2006 | Devane |
| 2007/0141147 | A1 | 6/2007 | Heil |
| 2007/0281021 | A1 | 12/2007 | McKinney |
| 2008/0132532 | A1 | 6/2008 | Wright |
| 2010/0010030 | A1 | 1/2010 | Jain |
| 2010/0040689 | A1 | 2/2010 | Hou |
| 2010/0092562 | A1 | 4/2010 | Hollenbeck |
| 2010/0249045 | A1 | 9/2010 | Babul |
| 2011/0065628 | A1 | 3/2011 | Johnson |
| 2014/0121279 | A1 | 5/2014 | Owen |

OTHER PUBLICATIONS

Darwish, Mona et al., Single- and Multiple-dose Pharmacokinetics of a Hydrocodone Bitartrate Extended-release Tablet Formulated with Abuse-deterrence Technology in Healthy, Naltrexone-blocked Volunteers, Clinical Therapeutics, vol. 37, No. 2, 2015, 12 pages.
Darwish, Mona, et al., Effects of Renal Impairment and Hepatic Impairment on the Pharmacokinetics of Hydrocodone After Administration of a Hydrocodone Extended-Release Tablet Formulated with Abuse-Deterrence Technology, ACCP, Clinical Pharmacology in Drug Development, 2015, 9 pages.
Darwish, Mona, et al., "Pharmacokinetics of Hydrocodone Extended-Release Tablets Formulated with Different Levels of Coating to Achieve Abuse Deterrence Compared with a Hydrocodone Immediate-Release/Acetaminophen Tablet in Healthy Subjects", Original Research Article, Nov. 13, 2014, 10 pages.
Non-Final Office Action in U.S. Appl. No. 14/978,302 dated Mar. 24, 2016, 8 pages.
Smith, Howard S., MD, Opioid Metabolism, Mayo Clinic Proceedings, Jul. 2009; 84(7), pp. 613-624.
Non-Final Office Action in U.S. Appl. No. 14/978,217 dated Mar. 24, 2016, 8 pages.
Final Office Action in U.S. Appl. No. 14/523,162, dated Jan. 25, 2016, 6 pages.
Final Office Action in U.S. Appl. No. 13/950,969, dated Jun. 22, 2015, 19 pages.
First Action Interview Pilot Program—Pre-Interview Communication in U.S. Appl. No. 14/815,219, dated Sep. 30, 2015, 5 pages.
Non-Final Office Action in U.S. Appl. No. 13/950,969, dated Dec. 18, 2015, 20 pages.
Non-Final Office Action in U.S. Appl. No. 13/950,969, dated Jan. 6, 2015, 19 pages.
Non-Final Office Action in U.S. Appl. No. 14/523,162, dated Sep. 30, 2015, 6 pages.
Non-Final Office Action in U.S. Appl. No. 14/523,162, May 7, 2015, 9 pages.
Non-Final Office Action in U.S. Appl. No. 14/815,219, dated Oct. 29, 2015, 5 pages.
Non-Final Office Action in U.S. Appl. No. 14/978,223, dated Feb. 25, 2016, 7 pages.
Bond, "Effects of renal impairment and hepatic impairment on the pharmacokinetics of hydrocodone after administration of a novel extended-release hydrocodone tablet formulated with OraGuardTM technology", Pain Week Accepted Abstracts, 2013.
Jonhson, "Opiod Safety in Patients With Renal or Hepatic Dysfunction", Pain Treatment Topics, Jun. 2007, pp. 1-9.

|  | Mild Impairment[1] | Moderate Impairment[2] | Severe Impairment[3] |
|---|---|---|---|
| HC-ER | | | |
| $C_{max}$ | 1.08 | 1.10 | ND[4] |
| $AUC_{0-inf}$ | 1.10 | 1.26 | ND |
| Oxycontin® (oxycodone hydrochloride extended release tablets)[5] | | | |
| $C_{max}$ | NR[6] | 1.5 | NR |
| AUC | NR | 1.95 | NR |
| Nucynta® ER (tapentadol extended oral-release tablets)[7] | | | |
| $C_{max}$ | 1.4 | 2.5 | NR |
| AUC | 1.7 | 4.2 | NR |
| Opana® ER (oxymorphone hydrochloride extended release tablets)[8] | | | |
| $C_{max}$ | NR | NR | NR |
| AUC | 1.6[9] | 3.7[9] | 12.2[9,10] |
| Exalgo® (hydromorphone hydrochloride extended release tablets)[11] | | | |
| $C_{max}$ | NR | ~4.0 | NR |
| AUC | NR | ~4.0 | NR |

Figure 1

| Demographic / Statistic | Mild Hepatic Impairment | Moderate Hepatic Impairment | No Hepatic Impairment | All Subjects |
|---|---|---|---|---|
| *No. of Subjects* | 10 | 10 | 10 | 10 |
| *Sex* | | | | |
| Male  n (%) | 7 (70.0%) | 8 (80.0%) | 7 (70.0%) | 22 (73.3%) |
| Female  n (%) | 3 (30.0%) | 2 (20.0%) | 3 (30.0%) | 8 (26.7%) |
| *Age (years)* | | | | |
| Mean (SD) | 56.1 (11.02) | 56.6 (4.60) | 56.8 (7.58) | 56.5 (7.89) |
| Median | 56.5 | 58.5 | 57.5 | 58.0 |
| Min / Max | 36, 75 | 47, 61 | 41, 65 | 36, 75 |
| *Age Group* | | | | |
| 18 – < 65 years | 8 (80.0%) | 10 (100%) | 7 (70.0%) | 25 (83.3%) |
| ≥ 65 – < 75 years | 1 (10.0%) | 0 (0%) | 3 (30.0%) | 4 (13.3%) |
| ≥ 75 years | 1 (10.0%) | 0 (0%) | 0 (0%) | 1 (3.3%) |
| *Weight (kg)* | | | | |
| Mean (SD) | 80.68 (16.15) | 87.89 (18.31) | 83.46 (13.60) | 84.01 (15.86) |
| Median | 79.65 | 86.75 | 84.00 | 82.15 |
| Min / Max | 58.8, 112.5 | 59.2, 113.6 | 65.5, 101.2 | 58.8, 113.6 |
| *Height (cm)* | | | | |
| Mean (SD) | 170.20 (8.53) | 172.20 (9.33) | 169.80 (8.60) | 170.73 (8.59) |
| Median | 169.00 | 173.50 | 171.00 | 171.00 |
| Min / Max | 159.0, 187.0 | 162.0, 188.0 | 156.0, 183.0 | 156.0, 188.0 |
| *BMI ($kg/m^2$)* | | | | |
| Mean (SD) | 28.07 (6.02) | 29.75 (6.31) | 28.89 (3.54) | 28.90 (5.29) |
| Median | 26.75 | 30.40 | 29.15 | 29.15 |
| Min / Max | 19.0, 38.9 | 22.0, 37.7 | 23.3, 34.6 | 19.0, 38.9 |
| *BMI Classification[1]* | | | | |
| Underweight: < 18.50 $kg/m^2$ | 0 (0%) | 0 (0%) | 0 (0%) | 0 (0%) |
| Normal: 18.50 – 24.99 $kg/m^2$ | 5 (50.0%) | 4 (40.0%) | 2 (20.0%) | 11 (36.7%) |
| Overweight: ≥ 25.00 $kg/m^2$ | 5 (50.0%) | 6 (60.0%) | 8 (80.0%) | 19 (63.3%) |
| Obese: ≥ 30.00 $kg/m^2$ | 4 (40.0%) | 5 (50.0%) | 4 (40.0%) | 13 (43.3%) |
| *Ethnicity* | | | | |
| Hispanic or Latino  n (%) | 6 (60.0%) | 2 (20.0%) | 5 (50.0%) | 13 (43.3%) |
| Not Hispanic or Latino n (%) | 4 (40.0%) | 8 (80.0%) | 5 (50.0%) | 17 (56.7%) |
| *Race* | | | | |
| American Indian or Alaskan Native n (%) | 0 (0%) | 0 (0%) | 0 (0%) | 0 (0%) |
| Asian  n (%) | 0 (0%) | 0 (0%) | 0 (0%) | 0 (0%) |
| Black, African American, or of African Heritage  n (%) | 1 (10.0%) | 1 (10.0%) | 2 (20.0%) | 4 (13.3%) |
| Native Hawaiian or Other Pacific Islander | 0 (0%) | 0 (0%) | 0 (0%) | 0 (0%) |
| White | 9 (90.0%) | 9 (90.0%) | 8 (80.0%) | 26 (86.7%) |
| Multiple Races Checked  n (%) | 0 (0%) | 0 (0%) | 0 (0%) | 0 (0%) |

Figure 2

| Pharmacokinetic Parameters | Subject Cohort | | |
|---|---|---|---|
| | Mild Hepatic Impairment N (%) | Moderate Hepatic Impairment N (%) | No Hepatic Impairment N (%) |
| PK Subjects | | | |
| Hydrocodone | | | |
| $C_{max}$ (ng/mL) | 24.0 (5.07) | 24.5 (5.03) | 22.1 (3.36) |
| $T_{max}$ (ng/mL) [1] | 6 (5–10) | 6 (5–8) | 6 (5–7) |
| $AUC_{0-inf}$ (ng*h/mL) | 439.6 (123.59) | 508.8 (156.94) | 391.3 (74.36) |
| AUC Extrapolated % (ng*h/mL) | 0.9 (0.5) | 1.1 (0.72) | 0.7 (0.31) |
| $T_{1/2}$ (hr) | 9.1 (1.55) | 9.9 (2.1) | 7.9 (1.54) |
| % Dose Excreted | 8.3 (2.36) | 9.5 (2.52) | 7.4 (2.46) |
| % Dose Excreted, Combined [2] | 17.8 (5.26) | 18.3 (3.29) | 18.2 (4.9) |
| Norhydrocodone | | | |
| $C_{max}$ (ng/mL) | 4.5 (0.82) | 3.7 (0.65) | 5.3 (1.37) |
| $T_{max}$ (ng/mL) | 5 (4–10) | 5 (4–10) | 5.5 (4–10) |
| $AUC_{0-inf}$ (ng*h/mL) | 92.7 (22.92) | 87.7 (16.42) | 115.9 (28.41) |
| AUC Extrapolated % (ng*h/mL) | 2.3 (0.93) | 3 (0.91) | 1.9 (0.67) |
| $T_{1/2}$ (hr) | 9.2 (1.79) | 11.4 (2.25) | 9 (1.45) |
| % Dose Excreted | 9.1 (3.3) | 8.4 (1.5) | 10.5 (3.61) |
| Hydromorphone | | | |
| $C_{max}$ (ng/mL) | 0.2 (0.09) | 0.3 (0.15) | 0.3 (0.16) |
| $T_{max}$ (ng/mL) | 6 (4–12) | 10 (5–24) | 12 (5 – 24) |
| $AUC_{0-inf}$ (ng*h/mL) | 8.3 (3.34) | 11.2 (4.63) | 14.4 (6.51) |
| AUC Extrapolated % (ng*h/mL) | 52.1 (23.77) | 42.1 (26.08) | 40.5 (28.2) |
| $T_{1/2}$ (hr) | 25.3 (12.54) | 25.1 (19.77) | 28.6 (26.35) |
| % Dose Excreted | 0.4 (0.18) | 0.4 (0.23) | 0.3 (0.2) |

Figure 3

TREATING PAIN IN PATIENTS WITH HEPATIC IMPAIRMENT

CROSS-REFERENCE

This application is a continuation of U.S. patent application Ser. No. 14/978,217, filed Dec. 22, 2015, which is a continuation of U.S. patent application Ser. No. 14/815,219 Jul. 31, 2015, now U.S. Pat. No. 9,265,760, which is a continuation of U.S. patent application Ser. No. 14/523,162 filed Oct. 24, 2014, which is a continuation in part of U.S. patent application Ser. No. 13/950,969 filed Jul. 25, 2013 which application claims the benefit of U.S. Provisional Application No. 61/677,601, filed Jul. 31, 2012 and U.S. Provisional Application No. 61/779,698, filed Mar. 13, 2013, which applications are incorporated herein by reference.

FIELD OF THE INVENTION

The present invention relates to a kit comprising an extended release composition for treating patients suffering from pain and hepatic impairment. In particular the present invention relates to a kit containing an extended release formulation of hydrocodone bitartrate, with no other active ingredients, packaged with a package insert that does not contain a warning, dose adjustment, or dosing table for patients presenting with mild or moderate hepatic impairment and further states that no adjustment in starting dose with Zohydro ER is required in patients with mild or moderate hepatic impairment. The present invention also relates to a method of treatment of a subject suffering from pain and hepatic impairment.

BACKGROUND OF THE INVENTION

Pain is a result of many medical conditions and procedures, and is the most common reason for physician visits in the United States. Pain can be acute, lasting until the source is removed or underlying condition heals, or it can be chronic, persisting for years. Acute pain can be caused by injury, stimulus of the nervous system, surgery, child birth, or "break-through pain" of a pain management regimen. Chronic pain can be caused by conditions such as cancer, arthritis, neuropathy, and can be idiopathic or psychogenic.

Opioids are a broad class of pharmaceuticals used clinically primarily for the treatment of pain. They are amongst the oldest known pharmaceuticals, and use of the opium poppy predates written history. The class includes morphine, codeine, hydrocodone, hydromorphone, oxycodone, tapentadol, naltrexone, fentanyl, sufentanyl and numerous others.

Hydrocodone is a semi-synthetic opioid derived from codeine and thebaine. It is commercially available in the United States as an oral tablet, capsule, suspension, syrup, or solution. Every hydrocodone product currently approved in the United States is in combination with another active ingredient. Products indicated for pain relief are combined with another analgesic such as acetaminophen, or less commonly ibuprofen, both of which can cause liver toxicity and are contraindicated in patients with hepatic impairment. The lack of a hydrocodone formulation without an additional active ingredient, and the lack of extended release hydrocodone formulations indicated for pain, limits the ability of physicians to treat pain in patients with hepatic impairment.

Opioids can be formulated in extended release formats to reduce dosing frequency and achieve more constant plasma levels. They are generally indicated for the continuous management of moderate to severe pain. Hydrocodone in combination with chlorpheniramine is available in a polistirex extended release capsule (Tussicaps®, Hi-Tech Pharma Co, also available as an oral suspension from Tris Pharma and UCB incorporated.) as a remedy for cold, flu, allergies, and other breathing illnesses, although there does not currently exist an approved hydrocodone extended release product indicated for pain.

Oxycodone hydrochloride is available as an extended release tablet (Oxycontin®, Purdue Pharma LP). Tapentadol hydrochloride is available as an extended release tablet (Nucynta® ER, Janssen Pharmaceuticals). Oxymorphone hydrochloride is available as an extended release tablet (Opana® ER, Endo Pharmaceuticals, also available from Actavis and Impax Labs). Morphine sulfate is available as extended release capsules (Avinza®, King Pharmaceuticals, Kadian®, Actavis, also available from Watson Labs), extended release capsules in combination with naltrexone (Embeda®, King Pharmaceuticals) and extended release tablets (MS Contin, Purdue Pharma, Oramorph®, Xanodyne Phamaceuticals, also available from Nesher Pharmaceuticals and Rhodes Pharmaceuticals). Hydromorphone hydrochloride is available as an extended release tablet (Exalgo®, Mallinkrodt). Hydromorphone hydrochloride extended release tablets (Palladone®, Purdue Pharma) were approved by the FDA in September of 2004 for continuous management of persistent, moderate to severe pain, but were taken off the market in July of 2005 due to serious and potentially fatal adverse reactions when taken with alcohol.

Hepatic impairment is a condition wherein normal functioning of the liver is reduced. Hepatic impairment can be acute, with rapid onset, or chronic. Chronic hepatic impairment, or cirrhosis, can occur from many causes, such as excessive consumption of alcohol, hepatitis, autoimmune disease, heredity, or metabolism, or can be idiopathic. Liver damage is generally irreversible, and treatment consists of prevention of progression and treatment of symptoms. In severe cases, liver transplant is the only option. Hepatic impairment can exhibit no significant symptoms, or may be characterized by such symptoms as reduced ability for the blood to clot (coagulopathy) and brain dysfunction (encephalopathy), fluid retention in the abdominal cavity, increased infection risk, hypogonadism, change in liver size, jaundice, and increased sensitivity to medication.

It is a problem that opioids, including extended release opioids, generally require reduced dosing in patients with hepatic impairment, because the liver is the source of most opioid metabolism. Using the same dosage in hepatically impaired patients as in those without hepatic impairment in general leads to higher $C_{max}$, higher AUCs, longer $t_{1/2}$, and can result in excessive or persistent sedation, coma or death. In a recent review (Johnson, S J. Opioid Safety in Patients with Renal or Hepatic Dysfunction, *Pain Treatment Topics*, June 2007), it was recommended that codeine, methadone, meperidine, and propxyphene not be used in patients with severe hepatic impairment. For hydromorphone and hydrocodone, the recommendation was to start with 50% of the usual dose, oxycodone ⅓ to ½ of the usual dose, and for morphine, the recommendation was to increase the dosing interval by twice the usual time period. In another recent article, (Bond, M., Effects of renal impairment and hepatic impairment on the pharmacokinetics of hydrocodone after administration of a novel extended-release hydrocodone tablet formulated with OraGuard™ technology, *Pain Week Accepted Abstracts,* 2013), it was found that the delivery of extended release hydrocodone without an immediate release component led to systemic exposure to hydrocodone that was ~70% higher in subjects with moderate hepatic impairment vs normal hepatic function. Mean hydrocodone AUC was 269 ng*hr/mL in subjects with moderate hepatic impairment, vs. 155 ng*hr/mL in subjects with normal hepatic function.

Similarly, opioid dosing of patients with hepatic impairment can lead to increases or decreases in the plasma levels, durations, and AUCs of metabolites.

Even mild and moderate hepatic impairment can lead to modified dosing requirements of opioids. FIG. 1 shows the measured increase $C_{max}$ and AUC of four approved extended release opioid products in mild and moderate hepatic impairment relative to subjects with no hepatic impairment, extracted from package inserts.

Extended release oxycodone (Oxycontin®, Purdue Pharma LP) was shown to have a $C_{max}$ increase of 1.5-fold compared to subjects without hepatic impairment, and an increase in AUC of 1.95-fold. The package insert has the following instruction: "A study of OxyContin in patients with hepatic impairment demonstrated greater plasma concentrations than those seen at equivalent doses in persons with normal hepatic function. Therefore, in the setting of hepatic impairment, start dosing patients at ⅓ to ½ the usual starting dose followed by careful dose titration. Data from a study involving 24 patients with mild to moderate hepatic dysfunction show peak plasma oxycodone and noroxycodone concentrations 50% and 20% higher, respectively, than healthy subjects. AUC values are 95% and 65% higher, respectively. Oxymorphone peak plasma concentrations and AUC values are lower by 30% and 40%. These differences are accompanied by increases in some, but not other, drug effects. The mean elimination $t_{1/2}$ for oxycodone increased by 2.3 hours."

Extended release tapentadol tablet (Nucynta® ER, Janssen Pharmaceuticals) was demonstrated to have an increase of 1.4-fold in $C_{max}$ and an increase of 1.7-fold in AUC for subjects with mild hepatic impairment, and an increase of 2.5- and 4.2-fold in $C_{max}$ and AUC respectively for those with moderate hepatic impairment. The package insert contained the following information: "NUCYNTA® ER has not been studied in patients with severe hepatic impairment. The use of NUCYNTA® ER in this population is not recommended. Use NUCYNTA® ER with caution in patients with moderate hepatic impairment. Initiate treatment in these patients using 50 mg NUCYNTA® ER and administer no more frequently than once every 24 hours. The maximum recommended dose for patients with moderate hepatic impairment is 100 mg of NUCYNTA® ER once daily. Administration of tapentadol resulted in higher exposures and serum levels to tapentadol in subjects with impaired hepatic function compared to subjects with normal hepatic function. The ratio of tapentadol pharmacokinetic parameters for the mild and moderate hepatic impairment groups in comparison to the normal hepatic function group were 1.7 and 4.2, respectively, for AUC; 1.4 and 2.5, respectively, for $C_{max}$; and 1.2 and 1.4, respectively, for $t_{1/2}$. The rate of formation of tapentadol-O-glucuronide was lower in subjects with increased liver impairment."

Extended release oxymorphone (Opana® ER, Endo Pharmaceuticals) was shown to have an increase in AUC of 1.6-fold and 3.7-fold in subjects with mild and moderate hepatic impairment, respectively, compared to subjects without hepatic impairment. The package insert contains the following: "The liver plays an important role in the presystemic clearance of orally administered oxymorphone. Accordingly, the bioavailability of orally administered oxymorphone may be markedly increased in patients with moderate to severe liver disease. The disposition of oxymorphone was compared in 6 patients with mild, 5 patients with moderate, and one patient with severe hepatic impairment and 12 subjects with normal hepatic function. The bioavailability of oxymorphone was increased by 1.6-fold in patients with mild hepatic impairment and by 3.7-fold in patients with moderate hepatic impairment. In one patient with severe hepatic impairment, the bioavailability was increased by 12.2-fold. The half-life of oxymorphone was not significantly affected by hepatic impairment . . . . Use OPANA ER with caution in patients with mild impairment, starting with the lowest dose and titrating slowly while carefully monitoring for side effects."

Extended release hydromorphone (Exalgo®, Mallinkrodt) demonstrated an approximately 4-fold increase in both $C_{max}$ and AUC in subjects with moderate hepatic impairment compared to subjects without hepatic impairment. The package insert contains the language "Start patients with moderate and severe hepatic . . . impairment on a reduced dose and closely monitor during dose titration. The pharmacokinetics of hydromorphone in severe hepatic impairment patients have not been studied. Further increase in $C_{max}$ and $AUC_{0-\infty}$ of hydromorphone in this group is expected, therefore, use an even more conservative starting dose."

Extended release morphine sulfate (Kadian®, Actavis) has the following information in its package insert: "Hepatic Failure: The pharmacokinetics of morphine were found to be significantly altered in individuals with alcoholic cirrhosis. The clearance was found to decrease with a corresponding increase in half-life. The M3G and M6G to morphine plasma AUC ratios also decreased in these patients indicating a decrease in metabolic activity . . . the increased risks associated with its use in the following populations should be considered: . . . those with severe impairment of hepatic . . . function. KADIAN® should be administered with caution, and in reduced dosages in . . . patients with severe . . . hepatic insufficiency."

The changes in pharmacokinetic parameters such as AUC, $C_{max}$, $t_{1/2}$ of a drug and/or its metabolites in patients with hepatic impairment can lead to many problems, including need for adjusting dose, complications for physicians in prescribing, need for liver function tests, lack of availability of correct doses, lack of availability of certain medications to those with hepatic impairment, and overdosing.

SUMMARY OF THE INVENTION

A kit for the treatment of pain is disclosed which kit is comprised of a plurality of oral dose units, each comprised of a pharmaceutically acceptable formulation comprising an analgesic which may consist only of hydrocodone (including pharmaceutically acceptable salt forms thereof) as the only pharmacologically active ingredient. The oral dosage units comprise a sustained release component and are formulated for the treatment of chronic pain, and are preferably formulated to treat pain which requires daily, around the clock, long term opioid treatment and for which alternative treatment options are inadequate. The kit includes a package which holds a plurality of oral dosage units and a package insert which provides dosing instructions for patients wherein the written instructions included in the kit apply equally to patient's with and without hepatic impairment, the written instructions explicitly stating that no adjustment in starting dose is required in patients with mild or moderate hepatic impairment relative to patients without such hepatic impairment. The dosage units are preferably comprised of a multiparticulate modified release composition comprising groups of particles which are comprised of a pharmaceutically acceptable carrier and hydrocodone as the sole pharmaceutically active ingredient. The kit provides a convenient, cost efficient method for treating pain in a wide range of patients without special consideration to those with hepatic impairment.

The oral dosage units are preferably comprised of an immediate release component and a sustained release component. Preferably the sustained release component comprises a controlled release polymer. Preferably the controlled release polymer is selected such that the release profile, as measured in a USP dissolution apparatus, is largely pH independent. Preferably the oral dosage units comprise an active ingredient that consists essentially only of a single opioid analgesic which is preferably hydrocodone, and specifically does not contain acetaminophen. Preferably the hydrocodone is in the form of hydrocodone bitartrate. Preferably, the sustained release component contains about 20% to about 95% of the hydrocodone, more preferably about 50% to about 90%, still more preferably about 75% to about 85%, most preferably about 80%. Preferably the immediate release component contains about 5% to about 80% of the hydrocodone, more preferably about 10% to about 50%, still more preferably about 15% to about 25%, most preferably about 20%. Preferably the oral dosage form comprises beads.

When placed in a USP dissolution apparatus buffered at a pH of about 6.8, about 10% to about 30% of the hydrocodone is released during the first hour, preferably about 15% to about 25%, more preferably about 16% to about 24%, most preferably about 21%. About 20% to about 40% of the hydrocodone is released in the first two hours, preferably about 24% to about 36%, more preferably about 25% to about 35%, most preferably about 30%. About 35% to about 65% of the hydrocodone is released in the first four hours, preferably about 40% to about 62%, more preferably about 45% to about 56%, most preferably about 51%. About 45% to about 80% of the hydrocodone is released in the first six hours, preferably about 50% to about 76%, more preferably about 55% to about 71%, most preferably about 63%. About 55% to about 95% of the hydrocodone is released in the first 8 hours, preferably about 60% to about 90%, more preferably about 65% to about 85%, most preferably about 75%. About 60% to about 98% of the hydrocodone is released in the first 12 hours, preferably about 65% to about 95%, more preferably 75% to about 95%, most preferably about 85%. The composition is designed to release hydrocodone in a way such that the increase in hydrocodone exposure in hepatically impaired patients, especially mildly or moderately hepatically impaired patients, is not clinically significant.

When placed in a USP dissolution apparatus buffered at a pH of about 6.8, the hydrocodone is released at an average rate of about 10%/hr to about 30%/hr during the first hour, preferably about 15%/hr to about 25%/hr, more preferably about 16%/hr to about 24%/hr, most preferably about 21%/hr. The hydrocodone is released at an average rate of about 5%/hr to about 15%/hr during the time period of from about 1 hour to about 4 hours, preferably about 7%/hr to about 11%/hr, more preferably about 8%/hr to about 10%/hr, most preferably about 9%/hr. The hydrocodone is released at a rate of about 5%/hr to about 10%/hr during the time period of from about 4 hours to about 6 hours, preferably about 6%/hr to about 9%/hr, more preferably about 7%/hr to about 8%/hr, most preferably about 7.5%/hr. The hydrocodone is released at a rate of about 2%/hr to about 8%/hr during a time period of from about 6 hours to about 8 hours, preferably about 3%/hr to about 7%/hr, more preferably about 4%/hr to about 6%/hr, most preferably about 5%/hr. The hydrocodone is released at a rate of about 0.5%/hr to about 4%/hr during a time period of from about 8 hours to about 12 hours, preferably about 1%/hr to about 3.5%/hr, more preferably about 2%/hr to about 3%/hr, most preferably about 2.5%/hr. The hydrocodone is released at a rate of about 3%/hr to about 9%/hr during a time period of from about 1 hours to about 12 hours, preferably about 4%/hr to about 8%/hr, more preferably about 4.5%/hr to about 6.9%/hr, most preferably about 6%/hr. The hydrocodone is released at a rate greater than 0%/hr and less than or equal to about 10%/hr during a time period of from about 4 hours to about 12 hours, preferably about 2%/hr to about 6%/hr, more preferably about 3%/hr to about 5%/hr, most preferably about 4%/hr.

Preferably each oral dosage unit comprises hydrocodone bitartrate in an amount from about 5 mg to about 80 mg, more preferably more than 10 mg and less than 60 mg, most preferably about 15 mg to about 50 mg. Preferably the the amount of hydrocodone bitartrate in each oral dosage unit is selected from 10 mg, 15 mg, 20 mg, 30 mg, 40 mg, and 50 mg, more preferably 15 mg, 20 mg, 30 mg, 40 mg, and 50 mg, still more preferably 15 mg, 20 mg, and 30 mg, still more preferably 20 mg and 30 mg, most preferably 20 mg. Preferably each oral dosage unit comprises 20 mg or more of hydrocodone bitartrate. Other salts of hydrocodone may similarly be used.

The release profile of the hydrocodone of the current invention is selected such that the average hydrocodone AUC per 20 mg of hydrocodone bitartrate dosed to subjects not suffering from renal or hepatic impairment is in the range of about 300 ng*h/mL to about 500 ng*h/mL, preferably from about 312 ng*h/mL to about 469 ng*h/mL more preferably from about 317 ng*h/mL to about 465 ng*h/mL, still more preferably about 343 ng*h/mL to about 391 ng*h/mL, most preferably about 391 ng*h/mL. The release profile of the hydrocodone of the current invention is selected such that the average Cmax per 20 mg of hydrocodone bitartrate dosed is in the range of about 17 ng/ml to about 27 ng/ml, preferably from about 18.7 ng/ml to about 25.3 ng/ml, more preferably from about 19 ng/ml to about 22 ng/ml, most preferably about 22 ng/ml.

The release profile of the hydrocodone of the current invention is selected such that the average AUC of hydrocodone per 20 mg of hydrocodone bitartrate dosed to subjects suffering from mild hepatic impairment is in the range of about 300 ng*h/mL to about 570 ng*h/mL, preferably from about 316 ng*h/mL to about 564 ng*h/mL more preferably from about 352 ng*h/mL to about 528 ng*h/mL, most preferably about 440 ng*h/mL. The release profile of the hydrocodone of the current invention is selected such that the average Cmax of hydrocodone per 20 mg of hydrocodone bitartrate dosed is in the range of about 19 ng/ml to about 29 ng/ml, preferably from about 19.2 ng/ml to about 28.8 ng/ml, most preferably about 24 ng/ml.

The release profile of the hydrocodone of the current invention is selected such that the average AUC of hydrocodone per 20 mg of hydrocodone bitartrate dosed to subjects suffering from moderate hepatic impairment is in the range of about 300 ng*h/mL to about 700 ng*h/mL, preferably from about 352 ng*h/mL to about 666 ng*h/mL more preferably from about 405 ng*h/mL to about 615 ng*h/mL, most preferably about 509 ng*h/mL. The release profile of the hydrocodone of the current invention is selected such that the average Cmax of hydrocodone per 20 mg of hydrocodone bitartrate dosed is in the range of about 20 ng/ml to about 30 ng/ml, preferably about 25 ng/ml.

The release profile of hydrocodone of the current invention is selected such that the increase in average AUC of hydrocodone in subjects suffering from mild hepatic impairment relative to subjects not suffering from renal or hepatic impairment is less than 60%, preferably less than 30%, more preferably less than or equal to about 14%. The release profile of hydrocodone of the current invention is selected such that the increase in average AUC of hydrocodone in subjects suffering from moderate hepatic impairment relative to subjects not suffering from renal or hepatic impairment is less than 70%, preferably less than 50%, more preferably less than or equal to about 30%.

The release profile of hydrocodone of the current invention is selected such that the increase in average cmax in subjects suffering from mild hepatic impairment relative to subjects not suffering from renal or hepatic impairment is less than 45%, preferably less than 25%, more preferably less than or equal to about 9%. The release profile of hydrocodone of the current invention is selected such that the increase in average cmax in subjects suffering from moderate hepatic impairment relative to subjects not suffering from renal or hepatic impairment is less than 50%, preferably less than 30%, more preferably less than or equal to about 14%.

The oral dosage unit may be comprised of a first group of immediate release, hydrocodone containing particles, and second, third, fourth etc. groups of sustained release hydrocodone containing particles. This allows for immediate release of a percentage of the hydrocodone from the first group and controlled release of the remaining hydrocodone in the oral dosage unit. The immediate release hydrocodone containing particles may contain from 5% to 50% by weight of the total weight of hydrocodone present. The sustained release hydrocodone containing particles may contain from 50% to 95% by weight based on the total weight of hydrocodone present. In a particularly preferred embodiment, the oral dosage form contains a first group or population of immediate release particles which may consist only of hydrocodone bitartrate, and a second group or population of sustained release particles. The second group may be particles substantially identical to the first group, but coated with a controlled release coating material, wherein the population of immediate release particles contains 15-25 percent of the total hydrocodone in the oral dosage form, more preferably 19-21 percent, still more preferably about 20 percent±10% of the 20% weight. It will be understand that upon reading, appreciating and understanding this disclosure, that other sustained release configurations can be used to achieve the same release and pharmacokinetic profiles.

The extended release formulation of the invention may be a multiparticulate modified release composition inside a capsule. That composition may be comprised of two different groups of particles where the first group is for immediate release which particles dissolve in five minutes or less. A second group of particles provides for controlled release. The second group of particles releases substantially no drug during the first hour. Thereafter, the second group of particles is dissolved such that the outer coating allows some of the drug to seep out into the surrounding solution. The drug seeps out over a period of time starting at about 1 hour after administration and continues until about 10-12 hours after administration. The rate of release is such that after considering the half-life of the drug the blood levels of the drug do not become dangerously high to a patient even when the patient is hepatically impaired and a government approved label packaged with the drug indicated the dosage can be administered to patients with and without hepatic impairment. However, the dissolution and pharmacokinetic profiles of the current invention can be achieved by other means, including single population particulates and non-particulate.

The invention includes a kit which is comprised of an extended release opioid formulation. The formulation may be in the form of pills or capsules and the pills or capsules are present within a package. The package includes an instruction which includes dosing instructions. The instruction may be written instructions in the form of a package insert which is required by a governmental agency such as the FDA in the United States. The instruction does not include a warning with respect to dosage adjustment and instructions or a dosing table for patients suffering from conditions such as mild hepatic impairment, moderate hepatic impairment or severe hepatic impairment. The instruction does not include dosing instructions or a dosing table directed specifically to patients suffering from mild hepatic impairment or moderate hepatic impairment. Preferably, the instruction specifically states that dose adjustment is not required for conditions selected from mild, moderate, or severe hepatic impairment. The instruction preferably includes language similar to "No adjustment in starting dose is required in patients with mild or moderate hepatic impairment". The opioid formulation may comprise a single pharmaceutically active ingredient which may be an opioid which may be hydrocodone. Preferably, the active ingredient of the formulation consists essentially only of hydrocodone bitartrate, and does not comprise acetaminophen. The extended release aspects of the formulation may come from a multiparticulate modified release composition which includes a plurality of dosage units with different populations of beads. For example, the formulation may include 15 to 25% of beads which provide for immediate release of the hydrocodone, a second population of 75 to 85% of the hydrocodone which provides for sustained release such that no hydrocodone is released from the second population until after 1 hour from administration and thereafter the release rate is such that a constant release rate of hydrocodone is provided over a period of 3 hours or more, 8 hours or more, or up to 12 hours.

In one embodiment of the invention the immediate release component comprises about 20% by weight of the hydrocodone±10% regarding the hydrocodone weight and the controlled release component makes up 80% by weight of the hydrocodone±10% wherein the weight percentages are based on the total weight of hydrocodone drug component in the formulation.

It is an object of the current invention to supply a method of treatment of pain in human patients with hepatic impairment.

It is a further object of the current invention to supply an opioid drug that is not currently available for the treatment of pain in human patients with hepatic impairment due to its only being available in combination with one or more additional active ingredients. In a preferred embodiment, the opioid or active drug component consists essentially only of hydrocodone.

It is a further object of the current invention to supply a formulation indicated for opioid treatment consisting essentially only of hydrocodone, i.e. wherein the formulation does not contain any other active ingredients. Specifically, the formulation does not contain any other pain or respiratory medications. More specifically, the medication does not contain acetaminophen, ibuprofen, chlorpheniramine, pseudoephedrine, homatropine, or salt forms thereof.

It is a further object of the invention to supply an extended release formulation for the treatment of pain. Preferably the formulation comprises an opioid, more preferably hydrocodone. In a preferred embodiment, the formulation does not contain any other active ingredients. In a more preferred embodiment, the extended release formulation comprises particulates, and preferably is a multiparticulate dosage form having two or more groups or populations of drug loaded beads, each of which group or population is adapted to release the drug at a different rate and which is designed to be delivered by the oral route. Preferably, the design of the formulation is such that it does not require a dosing adjustment, more preferably does not require an adjustment in starting dose, in patients with mild hepatic impairment. More preferably, the design of the formulation is such that it does not require a change in dosing, more preferably does not require an adjustment in starting dose in patients with mild or moderate hepatic impairment relative to patients without such hepatic impairment. Most preferably, it does not require a change in dosing for human patients with mild, moderate, or severe hepatic impairment.

It is a further object of the invention to supply a kit, comprising a drug in its primary packaging and a written instruction optionally contained within or attached to an optional secondary package. The instruction may be in the form of a written package insert. Preferably, the instruction does not contain a warning related to dosing patients with mild hepatic impairment. More preferably, the instruction does not contain a warning related to dosing patients with mild or moderate hepatic impairment, which warning is present with conventional hydrocodone oral dosing formulations. Most preferably, the instruction does not contain any warning related to hepatic impairment. Preferably, the instruction does not contain modified dosing instructions or dosing table related to dosing patients with mild hepatic impairment. More preferably, the instruction does not contain modified dosing instructions or dosing table related to dosing patients with mild or moderate hepatic impairment. Most preferably, the instruction does not contain any modified dosing instructions or dosing table related to hepatic impairment. Preferably, the instruction does not contain a requirement for adjusting the starting dose in patients with mild impairment. More preferably, the instruction does not contain a requirement for adjusting the starting dose in patients with mild or moderate hepatic impairment. Preferably, the instruction specifically states that dose adjustment is not required in patients with conditions selected from mild, moderate, or severe hepatic impairment. The instruction most preferably includes language similar to "No adjustment in starting dose is required in patients with mild or moderate hepatic impairment".

These and other objects, advantages, and features of the invention will become apparent to those persons skilled in the art upon reading the details of the formulations and methodology as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 is a table comparing impact on AUC and $C_{max}$ of hepatic impairment for four extended release opioid products and the current invention.

FIG. 2 is a table of demographic data for a study that was conducted using the current invention in human patients with no, mild, or moderate hepatic impairment.

FIG. 3 is a table of pharmacokinetic data for hydrocodone and its metabolites from the study shown in FIG. 2.

DETAILED DESCRIPTION OF THE INVENTION

Figure 4:
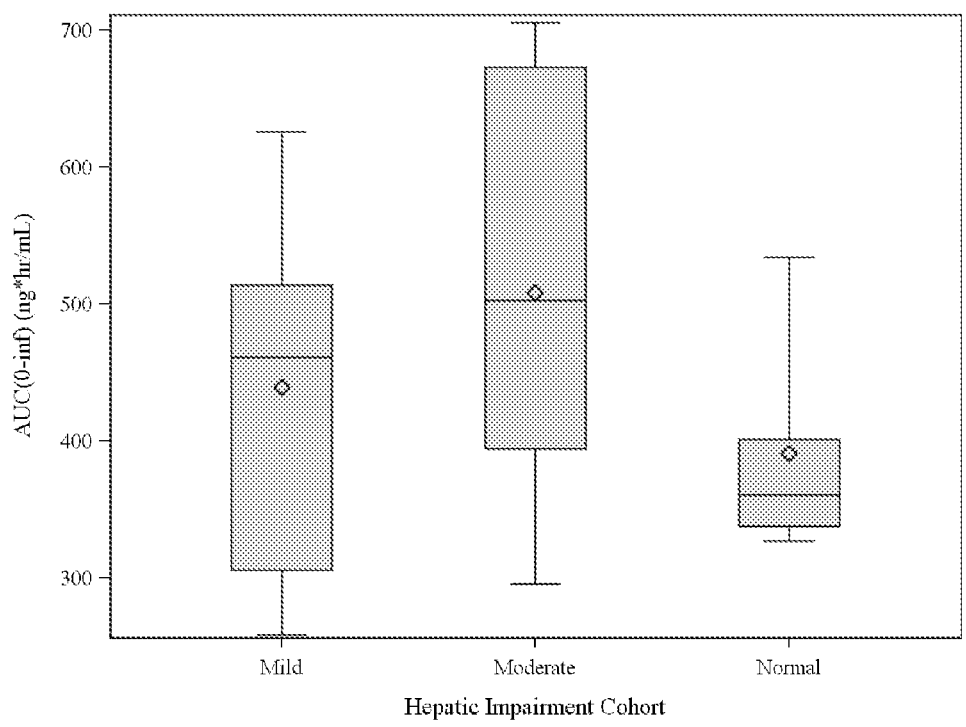
FIG. 4 is a "Box and Whiskers" plot graphically depicting the AUC data presented in FIG. 3. In the plot, the horizontal line represents the median; boxes represent 25th-75th percentiles; whiskers extend from the minimum to the maximum; Diamonds represent the mean.

Before the present formulations, kits and methods are described, it is to be understood that this invention is not limited to particular formulations, kits and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

When reference is made to an active pharmaceutical ingredient, unless stated otherwise it is to be taken to mean prodrugs; salt forms; metabolites; isomers; hydroxylated, glycosylated, oxidized, encapsulated, amorphous, or crystalline forms; thereof.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Active Pharmaceutical Ingredient, API, active ingredient, active drug substance, medicament, or the like: a component of a pharmaceutical formulation that is pharmaceutically active and is delivered for a desired effect.

Ascites: accumulation of peritoneal cavity fluid, most commonly due to severe hepatic impairment.

AUC: area under the curve, or the integral, of the plasma concentration of an API or metabolite over time following a dosing event. $AUC_{0-t}$ denotes the intregral under the plasma concentration curve from time 0 (dosing) to time "t". $AUC_{0-inf}$ or $AUC_{0-\infty}$ denotes the AUC from time zero to time infinity. Unless otherwise stated, AUC refers to $AUC_{0-inf}$. Often a drug is packaged in a salt form, for example hydrocodone bitartrate, and the dosage form strength refers to the mass of this salt form or the equivalent mass of hydrocodone bitartrate. However, plasma concentrations and AUC refer to the concentration of the pharmaceutically active component of the drug, not the drug salt.

Bilirubin: a yellow breakdown product of hemoglobin, often elevated in hepatic impairment. Elevated bilirubin leads to yellow discoloration of the skin, eyes, and mucous membranes, a condition known as jaundice.

Biodegradable: capable of chemically breaking down or degrading within the body to form nontoxic components. The rate of degradation of a depot can be the same or different from the rate of drug release.

Bulk erosion: the rate of water penetration into the depot exceeds the rate at which the depot is eroded (i.e. transformed into water soluble products)—leading to an erosion process that occurs throughout the entire volume of the depot—true with most hydrophilic polymers used in drug delivery currently.

Box and Whisker Plot: a way of graphically displaying data, wherein a horizontal line represents the mean, boxes denote the $25^{th}$-$75^{th}$ percentile range, "whiskers" or error bars extend from the maximum to the minimum, and a diamond shows the mean. Box and Whisker plots are useful for comparing treatment data from different cohorts, for example, differing levels of hepatic impairment, and analyzing data for clinical significance.

Child-Pugh Group, Child-Pugh Class, and the like: a ranking of level of hepatic impairment based on the Child-Pugh Score. Child-Pugh Scores of 5-6 are classified as Child-Pugh Class A (mild hepatic impairment) and have an expected 2 year survival rate of 85%. Child-Pugh Scores of 7-9 are classified as Child-Pugh Class B (moderate hepatic impairment) and have an expected 2 year survival rate of 57%. Child-Pugh Scores of 10-15 are classified as Child-Pugh Class C (severe hepatic impairment) and have an expected 2 year survival rate of 35%.

Child-Pugh Score: a score based on five clinical measures of hepatic impairment, including levels of total bilirubin, serum albumin, PT INR, ascites, and hepatic encephalopathy. Each measure is given a ranking of 1, 2, or 3, and the sum of the five rankings is the Child-Pugh Score. The Child-Pugh Score can be used to classify hepatic impairment by placing subjects in a Child-Pugh Group $C_{max}$: a pharmacokinetic parameter denoting the maximum observed blood concentration following delivery of an active pharmaceutical ingredient. $C_{max}$ occurs at the time of maximum plasma concentration, $T_{max}$. Often a drug is packaged in a pharmaceutically acceptable salt form, for example hydrocodone bitartrate, and the dosage for strength refers to the mass of this salt form or the equivalent mass of hydrocodone bitartrate. However, plasma concentrations, including $C_{max}$, refer the concentration of the pharmaceutically active component of the drug, not the drug salt.

Equivalent mass, dosage equivalent and the like: The mass of a commonly used salt form of an active pharmaceutical ingredient that has the same amount of drug as a mass of another, usually less commonly used salt form. For the current invention, the preferred pharmaceutically active ingredient is hydrocodone, which is most commonly provided in a pharmaceutically acceptable salt form, e.g. hydrocodone bitartrate. However, other salt forms or complexes may be used, for example hydrocodone polystirex. In order to reduce confusion and dosing errors, the dosage strength(s) of the less commonly used salt or complex forms will generally be denoted as hydrocodone bitartrate equivalents.

Extended release: the term "extended release" as used herein relates to the manner in which a pharmaceutically active ingredient is release from the formulation or dosage form in which it is contained. "Extended release" means that the duration of release of drug is prolonged as distinct from immediate release. The terms "extended release" and "sustained release" are used interchangeably herein. Similarly, the terms "controlled release" or "modified release" refer of release of pharmaceutically active ingredient from a composition or dosage form wherein the duration and/or rate of release is manipulated, modified or controlled in some manner so that the release of drug is not released immediately. The terms "extended release" and "sustained release" are encompassed by the terms "controlled release" and "modified release".

Dissolution: The percent release of active ingredient over time by an extended release dosage form when placed into a dissolution medium in a dissolution apparatus. Preferably the dissolution apparatus is one of the four dissolution apparatuses standardized and specified in United States Pharmacopoeia (USP) General Chapter <711> Dissolution, more preferably dissolution apparatus 2. Preferably the medium is water buffered at a pH of about 6.8.

Dissolution rate: The average percent rate of release of active ingredient over a specified time period when placed in a dissolution medium in a dissolution apparatus.

Formulation: any liquid, solid, or other state of matter that can be injected, taken orally, or delivered by another route as a pharmaceutical to a patient. Preferred formulations are for oral delivery. Preferably the formulations are designed for extended release delivery. Preferably the formulation is in the form of beads in a capsule. More preferably, the beads comprise an opioid analgesic and a modified or controlled release polymer, and, most preferably the active ingredient consists essentially only of hydrocodone. Formulations include but are not limited to those containing excipients that are suitable for oral delivery, and contain one or more active pharmaceutical ingredients, and preferably contain only one active pharmaceutical ingredient.

HC-ER, Zohydro ER™, and the like: hydrocodone bitartrate extended release capsules, a specific controlled release formulation comprising hydrocodone bitartrate in a multiparticulate modified release composition based on the Spheroidal Oral Drug Absorption System (SODAS®). (SODAS® is a registered trade mark of Alkermes Pharma Ireland Limited; Dublin, Ireland.) HC-ER does not contain any other active pharmaceutical ingredients other than hydrocodone.

Hepatic Impairment: hepatocellular (liver) dysfunction. Because many active pharmaceutical ingredients are metabolized in the liver, hepatic impairment can have statistically and clinically significant impact on pharmacokinetic parameters such as AUC, $C_{max}$, $T_{max}$, and $t_{1/2}$ of active pharmaceutical ingredients and their metabolites.

Hepatic Encephalopathy: increased levels of confusion, altered level of consciousness, and coma associated with hepatic impairment.

Human Serum Albumin, (HSA): a monomeric protein made in the liver that is the most common protein in animal plasma. Albumin levels can be reduced in hepatic impairment.

Hydrocodone: a semisynthetic narcotic analgesic and antitussive with multiple actions similar to those of codeine. Hydrocodone is an ingredient in prescription analgesics and cough medicines. Hydrocodone is usually supplied in a salt form, most often as hydrocodone bitartrate. However, other forms may be used, such as hydrocodone polystirex, in which case the amount of drug may be treated as an equivalent mass of hydrocodone bitartrate.

Package Insert, Prescribing Information, Patient Information Leaflet, P.I., or the like: a document provided in a kit along with a medication and its packaging to provide information about the drug. Package inserts are approved by a regulatory body chosen from the U.S. Food and Drug Administration, the European Medicines Agency, the Japanese Pharmaceuticals and Medical Devices Agency, the Australian Therapeutic Goods, Administration, or Health Canada. Package inserts can include warning, dosing information and tables, dosing recommendations for specific patient populations, and clinical trial experience. Preferably, the package insert does not contain a warning related to dosing patients with mild hepatic impairment. More preferably, in accordance with a kit of the invention the package insert does not contain a warning related to dosing patients with mild or moderate hepatic impairment. Most preferably, in accordance with a kit of the invention the package insert does not contain any warning related to hepatic impairment. Preferably, the package insert does not contain a modified dosing instruction or dosing table related to dosing patients with mild hepatic impairment. More preferably, in accordance with a kit of the invention the package insert does not contain a modified dosing instruction or dosing table related to dosing patients with mild or moderate hepatic impairment. Most preferably, in accordance with a kit of the invention the package insert does not contain any a modified dosing instruction or dosing table related to hepatic impairment. Preferably, the package insert does not contain a requirement for adjusting the starting dose in patients with mild impairment. More preferably, the package insert does not contain a requirement for adjusting the starting dose in patients with mild or moderate hepatic impairment. Preferably, the package insert specifically states that dose adjustment is not required in patients with conditions selected from mild, moderate, or severe hepatic impairment. The package insert most preferably includes language similar to "No adjustment in starting dose is required in patients with mild or moderate hepatic impairment".

Primary package, primary packaging, and the like: the container in direct contact with the formulation, capsule, tablet, etc.

PT INR, prothrombin time International normalized ratio, and the like: a measure of the ability of blood to clot. Elevated PT INR can be an indication of hepatic impairment.

Secondary package: a box, bag or other container that contains the drug in its primary packaging, and also contains or is attached to the package insert.

SODAS®, Spheroidal Oral Drug Absorption System: is a multiparticulate modified release drug delivery technology involving the production of substantially uniform spherical beads typically of about 1 to 2 mm in diameter containing drug plus excipients and coated with one or more product-specific modified-release polymers. Varying the nature and combination of polymers facilitates varying degrees of modified release depending upon the required product profiles. Modified release is achieved when the soluble polymers dissolve leaving pores within the outer membrane. Fluid then enters the core of the beads and dissolves the drug. The resultant solution diffuses out in a controlled, predetermined manner allowing for prolongation of the in vivo dissolution phase. Modified release may also be a result of the use of pH-dependent coatings or a single polymer system. Once produced, the beads are formulated into the final dosage form. Combing different populations of beads, each population exhibiting different degrees of modified-release gives rise to tailored drug-release profiles, making SODAS® technology a highly flexible and predictable oral drug delivery system. By employing two or more different populations of drug loaded beads, each with its own specific release characteristics an active ingredient may be delivered in a pulsed or bimodal manner. In this embodiment the multiparticulate modified release composition may comprise (or consist only of) an immediate release component and a modified release component; the immediate release component comprising (or consist only of) a first population of active ingredient containing beads and the modified release component comprising (or consist only of) a second population of active ingredient containing beads coated with a controlled release polymeric coating sufficient to achieve a pulse of the active ingredient following a time delay.

Multiparticulate Modified Release Composition: a composition containing a large number of small particles. The particles are made up of two or more groups of particles drawn from two or more populations, the groups or populations having different release properties. The particles may be comprised completely of drug, but preferably comprise drug in combination with one or more pharmaceutically acceptable carrier or excipient components. The SODAS® drug delivery technology is one example of a multiparticulate modified release approach. A multiparticulate modified release composition may include 2, 3 or any number of groups of particles wherein each group of particles includes a large number of particles such as 50, 100, or 200 or more particles which are each substantially identical to each other but which are each different from particles within the other groups. Thus, a first group may include particles consisting only of drug or consisting of drug and excipient material wherein the particles provide for immediate release such that the drug is released into solution immediately or within the first 30 minutes of less of administration, preferably within the first 15 minutes, more preferably within the first 5 minutes. A second group of particles may be designed in a manner similar to the immediate release particles, but are coated with an additional excipient material or materials such that the particles do not begin to release drug for some period of time such as 30 minutes to 2 hours after administration. A third group of particles may be present with thicker coatings which maintain all of the drug inside for a longer period of time as compared to the second group of particles. In principle, any desired release profile or pharmacokinetic profile can be achieved by the right combinations of groups of particles. By including multiple groups of particles it is possible to design the formulation such that sufficient drug is released to the patient to manage pain whereas insufficient drug is released so as to result in dangerously high blood levels even for patients who are hepatically impaired.

Multiparticulate Modified Release Dosage Form: A dosage form comprising a multiparticulate modified release composition.

Surface Erosion: the rate of water penetration into the depot is slower than the rate at which the depot is eroded—the depot erodes from the surface before water has penetrated the entire volume of the device.

$T_{max}$: a pharmacokinetic parameter denoting the time to maximum blood concentration following delivery of an active pharmaceutical ingredient $t_{1/2}$, plasma half-life, elimination half-life, or the like: A pharmacokinetic parameter denoting the apparent plasma terminal phase half-life, i.e. the time, after absorption and distribution of an API is complete, for the plasma concentration to fall by half.

Invention in General

The current invention is a kit, formulation and method indicated for continuous management of moderate to severe pain. The formulation comprises an analgesic, preferably an opioid analgesic. Preferably the formulation comprises components designed to achieve both an immediate release and an extended release delivery profile, and more preferably the formulation comprises a multiparticulate modified release Multiparticulate Modified Release Composition. The invention can be applied to any delivery methodology or route, including pulmonary, parenteral, transdermal, buccal, anal, or vaginal, but is preferably delivered by the oral route. The formulation preferably takes the form of groups of beads in a capsule, preferably a gelatin capsule. The capsule is preferably swallowed whole, but can also be opened and the beads in the form of two or more groups of beads may be sprinkled on soft food that does not require chewing such as applesauce for those that have trouble swallowing the capsule.

Figure 6:
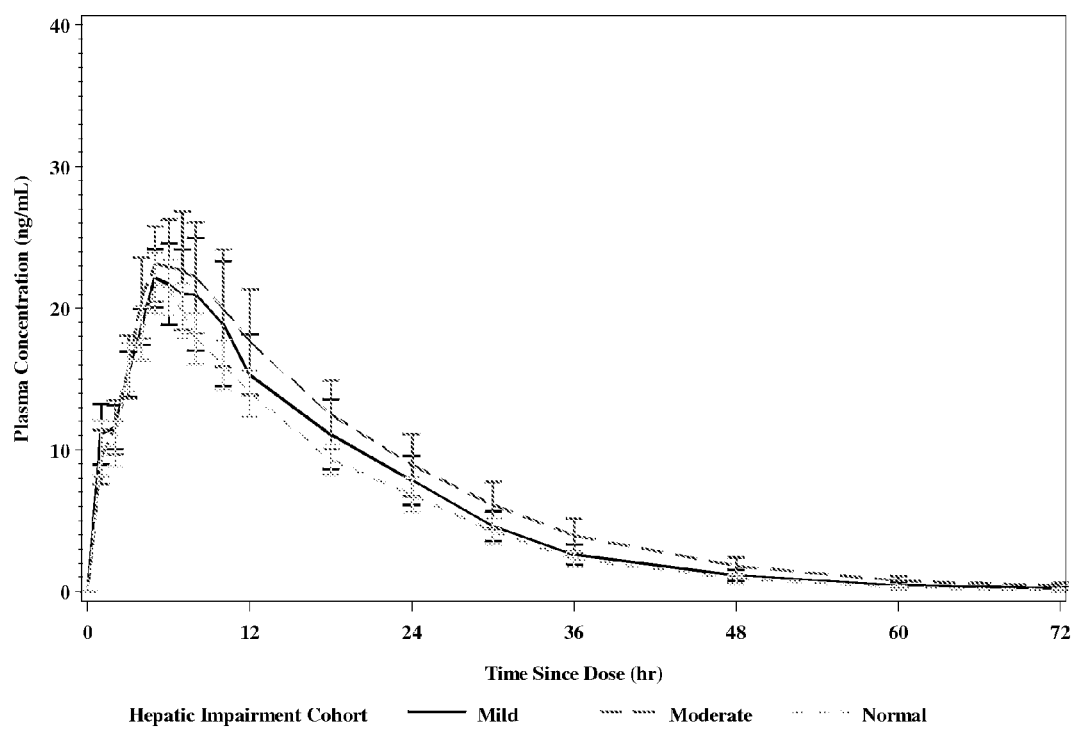
FIG. 6 is a plot of plasma concentration vs. time of Hydrocodone after administration of HC-ER also referred to here as Zohydro ER™.

The basic concept of the invention can be seen when viewing FIG. 6 and understanding the results shown there. Specifically, a formulation is provided to three different groups of patients where one group has normal liver function and one group has mild hepatic impairment and yet another group has moderate hepatic impairment. The results show that although there are some differences in terms of the blood plasma levels obtained, the differences are small and the blood levels are actually very similar pharmacologically. Thus, when using a formulation of the type described here no separate dosing instructions need be given with respect to patients with and without hepatic impairment. In fact, if lower doses are given to patients with hepatic impairment (compared to normal patients) the patient may not receive adequate drug levels and as such the patient's pain will not be adequately controlled.

In a particularly preferred embodiment, referred to here as HC-ER, the formulation comprises an extended release formulation of hydrocodone, with no other active ingredients. Specifically, the formulation does not contain any other pain or respiratory medications. More specifically, the medication does not contain acetaminophen, ibuprofen, chlorpheniramine, pseudoephedrine, homatropine, or salt forms thereof and as such the active ingredient of the formulation consists essentially of hydrocodone.

The current invention supplies a method of treatment of pain for those with hepatic impairment. Because the current invention only contains hydrocodone and no other active ingredients, and most importantly does not contain acetaminophen, it will not be contra-indicated in patients with hepatic impairment.

Figure 5:
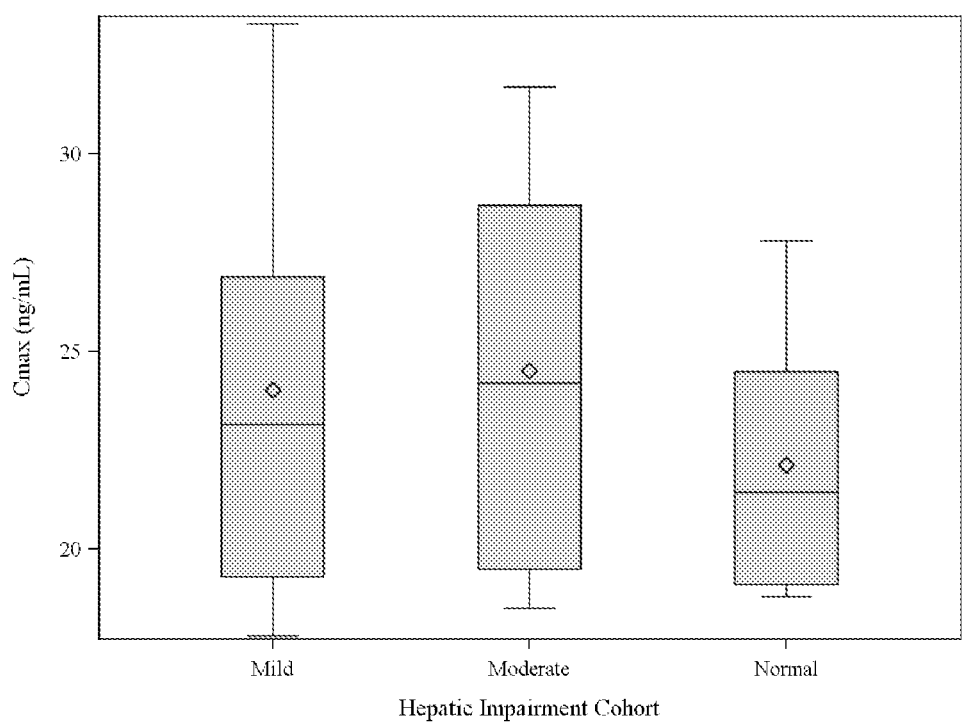
FIG. 5 is a "Box and Whiskers" plot graphically depicting the $C_{max}$ data presented in FIG. 3. In the plot, the horizontal line represents the median; boxes represent 25th-75th percentiles; whiskers extend from the minimum to the maximum; diamonds represent the mean.

It has been found that pharmacokinetic parameters such as $C_{max}$, $T_{max}$, AUC, and $t_{1/2}$ of hydrocodone are only slightly impacted by hepatic impairment when delivered in a multiparticulate modified release dosage form (see FIG. 3 and examples below). As can be seen in FIGS. 4 and 5, there is significant overlap of the 25%-75% confidence intervals and the minimum to maximum range for $C_{max}$ and AUC, showing that inter-subject variability is much larger than any variation due to level of hepatic impairment. This is also reinforced by the plasma concentration curves as shown in FIG. 6. Any difference due to level of hepatic impairment is not found to be clinically significant. This is quite surprising and non-obvious, especially given recommendations in the literature to dose patient with hepatic impairment at 50% of the normal dose (Johnson, S J. Opioid Safety in Patients with Renal or Hepatic Dysfunction, *Pain Treatment Topics*, June 2007)

These results for HC-ER are compared to existing extended release opioid products for which pharmacokinetic data are available in FIG. 1, including extended release tablet formulations of Oxycodone, Tapentadol, Oxymorphone, and Hydromorphone. Although slight increases in $C_{max}$ and AUC were measured with HC-ER in patients with mild and moderate hepatic impairment, in all cases these increases are small, and significantly smaller than the similar increases seen with the other extended release opioids.

Preferably, the design of the formulation is such that it does not require a warning (such as on the regulatory agency approved label or package insert) or dosing adjustment for patients with mild hepatic impairment. More preferably, the design of the formulation is such that it does not require a warning or change in dosing for patients with mild or moderate hepatic impairment. Most preferably, it does not require a warning or change in dosing for patients with mild, moderate, or severe hepatic impairment.

It is another key aspect of invention to supply a kit, comprising drug formulation in its primary packaging and a package insert, and an optional secondary package. Preferably, the drug is an analgesic, more preferably an opioid, most preferably hydrocodone. Preferably, the formulation comprises an extended release component, more preferably a multiparticulate modified release composition. Preferably the package insert does not contain a warning related to dosing patients with mild hepatic impairment. More preferably, the package insert does not contain a warning related to dosing patients with mild or moderate hepatic impairment. Most preferably, the package insert does not contain any warning related to hepatic impairment. Preferably, the package insert does not contain a modified dosing instruction or dosing table related to dosing patients with mild hepatic impairment. More preferably, the package insert does not contain a modified dosing instruction or dosing table related to dosing patients with mild or moderate hepatic impairment. Most preferably, the package insert does not contain any a modified dosing instruction or dosing table related to hepatic impairment. In a most preferred embodiment, the kit comprises a oral formulation of hydrocodone bitartrate with no other active ingredients in a multiparticulate modified release dosage form, wherein the hydrocodone bitartrate is in the form of different populations of drug loaded beads presented in a gelatin capsule, a primary package, and a package insert that does not have dosing adjustment instructions or a dosing table for patients with mild or moderate hepatic impairment. Each different population of beads is adapted so as to provide rates of drug release which differ from one bead group to another bead group. For example, a first group of beads may provide immediate release of the drug and a second bead group may provide no immediate release of drug and a controlled release beginning within one hour of administration and continuing to release drug at a constant rate over the following two to eight hours.

Preferably, the kit contains written instructions which include instructions related to dosing. Preferably, the instruction does not contain a requirement for adjusting the starting dose in patients with mild hepatic impairment. More preferably, instruction does not contain a requirement for adjusting the starting dose in patients with mild or moderate hepatic impairment. Preferably, the instruction specifically states that dose adjustment is not required in patients with conditions selected from mild, moderate, or severe hepatic impairment. The instruction most preferably includes language similar to "No adjustment in starting dose is required in patients with mild or moderate hepatic impairment".

The invention further encompasses a method of treatment of a patient suffering from chronic pain and hepatic impairment, the method comprising: presenting the patient with extended release formulation comprising an opioid analgesic and a package insert that does not contain an instruction for dosage adjustment or dosing table for patients with mild hepatic impairment, preferably a package insert that does not contain an instruction for dosage adjustment, or dosing table for patients with mild or moderate hepatic impairment, more preferably a package insert that does not contain a warning, instruction for dosage adjustment, or dosing table for patients with hepatic impairment.

The invention further encompasses a package insert for an opioid product, preferably an extended release opioid product, more preferably an extended release hydrocodone product, most preferably a multiparticulate modified release composition hydrocodone product, wherein the package insert does not contain an instruction for dosage adjustment or dosing table for patients with mild hepatic impairment, preferably the package insert does not contain an instruction for dosage adjustment or dosing table for patients with mild or moderate hepatic impairment, more preferably the package insert that does not contain a warning, instruction for dosage adjustment, or dosing table for patients with hepatic impairment.

An example of a portion of a label the instruction that may be used connection with the present invention is provided below, the tradename of HC-ER in this example is Zohydro ER:

Indications and Usage

Zohydro™ ER (hydrocodone bitartrate) is indicated for the management of pain severe enough to require daily, around-the-clock, long-term opioid treatment and for which alternative treatment options are inadequate. Zohydro ER is not indicated as an as-needed (prn) analgesic.

Dosage and Administration

For opioid-naïve and opioid non-tolerant patients, initiate with 10 mg capsules orally every 12 h. To convert to Zohydro ER from another opioid, use available conversion factors to obtain estimated dose. Increase the dose of Zohydro ER in increments of 10 mg every 12 hours every 3 to 7 days as needed to achieve adequate analgesia. Individualize treatment; titrate to effective and tolerable dose. Capsules must be swallowed whole and are not to be chewed, crushed or dissolved.

Dosage Forms and Strengths

Extended-release capsules: 10 mg, 15 mg, 20 mg, 30 mg, 40 mg and 50 mg

Use in Specific Populations

Hepatic impairment: No adjustment in starting dose with Zohydro ER is required in patients with mild or moderate hepatic impairment.

Renal impairment: Use a low initial dose of Zohydro ER in patients with renal impairment and monitor closely for adverse events such as respiratory depression.

Pharmacokinetics

As compared to immediate-release hydrocodone combination products, Zohydro ER at similar daily doses results in similar overall exposure but with lower maximum concentrations. The half-life is also longer due the prolonged duration of absorption. Based on the half-life of hydrocodone, steady-state should be obtained after 3 days of dosing. Following 7 days of dosing, AUC and Cmax increase approximately two-fold as compared to the first day of dosing. The pharmacokinetics of Zohydro ER have been shown to be independent of dose up to a dose of 50 mg. Zohydro ER capsules exhibit peak plasma concentrations occurring approximately 5 hours after dose administration.

Hepatic Impairment

After a single dose of 20 mg Zohydro ER in 20 patients with mild to moderate hepatic impairment based on Child-Pugh classifications, mean hydrocodone Cmax values were 25±5, 24±5, and 22±3.3 ng/mL for moderate and mild impairment, and, normal subjects, respectively. Mean hydrocodone AUC values were 509±157, 440±124, and 391±74 ng*h/mL for moderate and mild impairment, and, normal subjects, respectively. Hydrocodone Cmax values were 8-10% higher in patients with hepatic impairment while hydrocodone AUC values were 10% and 26% higher in patients with mild and moderate hepatic impairment, respectively.

Formulations of the invention are used for pain management using hydrocodone as the only active ingredient. The compositions and dosage forms of the present invention may provide continuous analgesia for up to 24 hours by providing minimum peak to trough fluctuations in plasma levels and be administered to all degrees of hepatic impairment.

The controlled release population(s) of particles used in the invention may be particles of drug coated with a material that allows for release of the drug at a desired rate. The coating materials may be polymer coating materials, such as cellulose acetate phthalate, cellulose acetate trimaletate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the trademark Eudragit® S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (m. wt. ~5 k-5,000 k), polyvinylpyrrolidone (m. wt. ~10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. ~30 k-300 k), polysaccharides such as agar, acacia, karaya, tragacanth, algins and guar, polyacrylamides, Polyox® polyethylene oxides (m. wt. ~100 k-5,000 k), AquaKeep® acrylate polymers, diesters of polyglucan, crosslinked polyvinyl alcohol and poly N-vinyl-2-pyrrolidone, sodium starch glycolate (e.g. Explotab®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof.

Excipients such as plasticizers, lubricants, solvents and the like may be added to the coating. Suitable plasticizers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Formulations of the invention comprise an active ingredient, a group of inactive ingredients in which the active ingredient is intermixed and a coating of inactive ingredients. The active ingredient may consist only of hydrocodone bitartrate in an amount of 10, 15, 20, 30, 40, 50, 60, 70 or 80 mg. The inactive ingredient may be comprised of a sugar, a polymer, and silicon dioxide and talc. The coating may be comprised of a polymer, silicon dioxide, talc, dyes and coloring agents in a gelatin capsule.

Example 2

A capsule of the invention contains an active ingredient in an amount selected from the group consisting of 10, 15, 20, 30, 40, 50, 60, 70 or 80 mg of hydrocodone bitartrate USP and the following inactive ingredients: sugar spheres NF, hypromellose 2910 USP, ammonio methacrylate copolymer Type B NF, silicon dioxide NF, and talc USP. The capsule shells collectively contain titanium dioxide, FD&C Blue #1, FD&C Red #40, FDA Yellow iron oxide, FD&C Red #3, FDA Black iron oxide, FDA Red iron oxide, and gelatin.

Example 3

A capsule of the invention may comprise an active ingredient of hydrocodone bitartrate USP in an amount in a range of 10 mg to 80 mg of hydrocodone bitartrate. The active ingredient is mixed with inactive ingredients, comprising:
sugar spheres NF,
hypromellose 2910 USP,
ammonio methacrylate copolymer Type B NF,
silicon dioxide NF, and
talc USP.
The capsule shell, comprises:
titanium dioxide,
FD&C Blue #1,
FD&C Red #40,
FDA Yellow iron oxide,
FD&C Red #3,
FDA Black iron oxide,
FDA Red iron oxide, and
gelatin.

Example 4

A capsule of the invention may contain beads comprising an active ingredient consisting essentially only of hydrocodone bitartrate, 5% to 60% by weight, controlled release polymers 0%-30% by weight, and other excipients, 25%-95% by weight. All weight amounts are based on the percentage of the total weight of the beads in the capsule which the total weight of the component makes up.

Example 5

A capsule of the invention may comprise an opioid, 5% to 60% by weight, mixed with inactive ingredients 25% to 95% by weight, and mixed with controlled release ingredients 0% to 30% by weight. All weight amounts are based on the percentage of the total weight of the beads in the capsule which the total weight of the component makes up.

Example 6

Multiparticulate Modified Release Composition Containing Hydrocodone Bitartrate

Multiparticulate modified release hydrocodone compositions used with the present invention may have an immediate release component and a modified release component. The immediate release component may be particles consisting only of drug such as hydrocodone bitartrate particles. The controlled release particle component may those particles coated with a coating which may be prepared according to the formulations shown in Tables 1 and 2.

Tables 1 and 2 show that immediate release formulations (Table 1) include drug and excipient materials which allow the drug to be readily dispersed and released upon administration. The immediate release particles can be any size and shape. However, they are generally spherical and have a diameter in a range of from about 5 to 50 microns.

The controlled release particles may use the immediate release particles and coat them. However, the controlled release particles may be prepared using drug and other excipient materials in order to integrate the polymeric excipient materials with the drug that form beads. These beads may also be of any size and shape. However, the beads are generally spherical and have a diameter in a range of from 5 to 50 microns.

Those skilled in the art will understand that larger particles dissolve more slowly as compared to smaller particles. Thus, one mechanism of controlling the release of the drug is to provide groups of particles which vary in size. This is done in a manner so as to reduce the height of the peaks of release rate and increase the troughs representing lower release rates thereby providing a more constant release to the patient. An overall objective is to provide a formulation which can be sold without warnings relating to dosing even when sold to patients which have various degrees of hepatic impairment.

Some non-limiting examples of immediate release (Table 1) and controlled release (Table 2) formulations are provided below.

TABLE 1

Immediate Release Component Hydrocodone Solutions

| | Amount, % (w/w) | | | | | |
|---|---|---|---|---|---|---|
| Ingredient | (i) | (ii) | (iii) | (iv) | (v) | (vi) |
| Hydrocodone Bitartrate | 6.0 | 6.0 | 6.0 | 6.0 | 6.0 | 6.0 |
| HPMC 2910 | 1.0 | 2.0 | 2.0 | — | — | 1.5 |
| Polyethylene Glycol 6000 | — | — | — | 0.5 | — | — |

TABLE 1-continued

Immediate Release Component Hydrocodone Solutions

| | Amount, % (w/w) | | | | | |
|---|---|---|---|---|---|---|
| Ingredient | (i) | (ii) | (iii) | (iv) | (v) | (vi) |
| Povidone K30 | — | — | — | — | 5.0 | — |
| Fumaric Acid | — | 6.0 | — | — | — | — |
| Citric Acid | — | — | 6.0 | — | — | — |
| Silicon Dioxide | 1.5 | 1.0 | 1.0 | — | — | 2.0 |
| Talc | 1.5 | — | — | — | — | — |
| Purified Water | 90.0 | 85.0 | 85.0 | 93.5 | 89.0 | 90.5 |

TABLE 2

Modified Release Coating Solutions

| | Amount, % (w/w) | | | | | | |
|---|---|---|---|---|---|---|---|
| Ingredient | (i) | (ii) | (iii) | (iv) | (v) | (vi) | (vii) |
| Eudragit RS 100 | 4.1 | 4.9 | 5.5 | 4.4 | — | 5.5 | 7.5 |
| Eudragit RL 100 | — | 0.5 | — | 1.1 | — | — | — |
| Eudragit L 100 | 1.4 | — | — | — | — | — | — |
| Ethocel | — | — | — | — | 3.0 | — | — |
| Triethyl Citrate | 1.5 | 1.6 | — | 1.1 | — | — | 1.5 |
| Dibutyl Sebacate | — | — | — | — | 0.6 | 1.0 | — |
| Silicon Dioxide | 1.0 | 1.0 | 1.0 | — | 2.0 | 1.0 | — |
| Talc | 2.5 | 2.5 | 1.0 | 2.8 | — | 1.0 | 2.5 |
| Acetone | 34.0 | 34.0 | 15.0 | 35.6 | — | 14.0 | 33.5 |
| Isopropyl Alcohol | 50.0 | 50. | 72.5 | 50. | 94.4 | 72.5 | 50.0 |
| Purified Water | 5.5 | 5.5 | 5.0 | 5.0 | — | 5.0 | 5.0 |

In these exemplary hydrocodone formulations, sugar spheres (30/35 mesh) may be provided as inert cores that act as a substrate for the active ingredient and other excipients present in the formulation. The quality and size selected reflect the requirement to produce particles with a mean diameter in the size range 0.5-0.6 mm to facilitate the subsequent coating processes for addition of the active pharmaceutical ingredient or modified release coating. Hydroxypropylmethylcellulose (2910) (Methocal E6 Premium LV) is used to prepare the immediate-release coating solution that may be used to coat the sugar spheres to produce the IR beads and acts as a binding agent. Silicon Dioxide (Syloid 244FP) is an anti-adherent that may be used in the preparation of the IR coating solution (Table 1) and the modified release coating suspension (Table 2). Ammonio methyacrylate copolymer Type B (Eudragit RS 100) is a rate-controlling polymer that imparts the controlled release properties to the formulation and exhibits pH independent release properties. Talc (Altalc 200) may be used as an anti-adherent in the modified-release coating process to manufacture the modified release beads. Acetone and isopropyl alcohol may be the two solvents in which the rate-controlling polymer may be dissolved to produce the coating suspension that may be applied to the IR beads to form the modified release beads. The resultant coating suspension is applied to the IR beads to form the modified release beads. Modified release beads may be dried in an oven for 10-20 hours at 40-500 C/30-60% RH to remove residual solvents and to obtain a moisture content of about 3-6%. Other processing procedures are further detailed in US2006/0240105 and U.S. Pat. No. 6,066,339 which is incorporated herein by reference in its entirety.

Example 7

Figure 7:
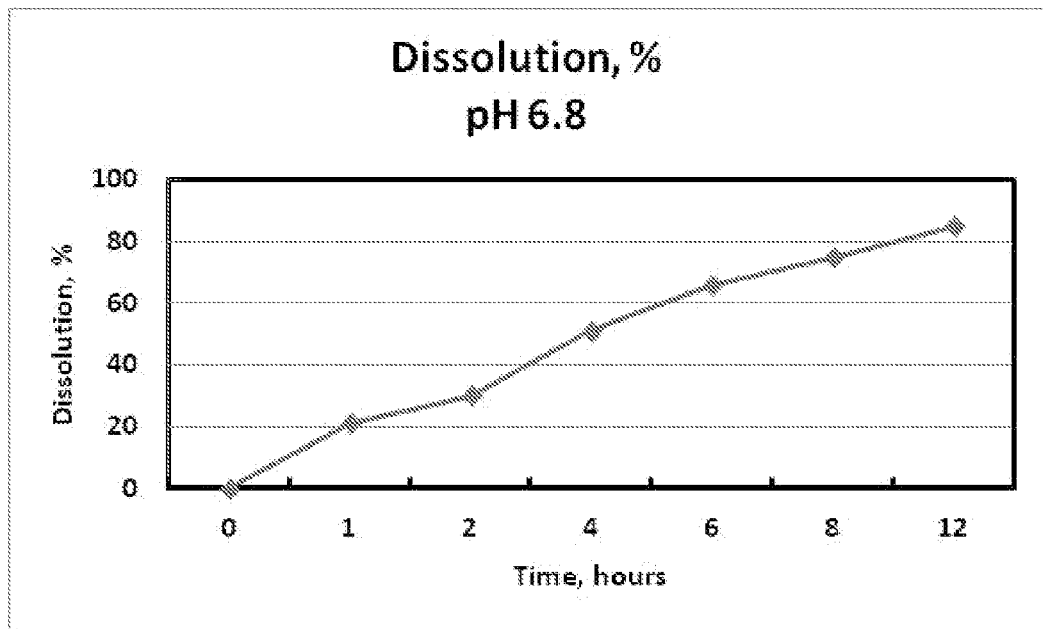
FIG. 7 is a plot of percent hydrocodone released over time from an embodiment of the current invention when placed in a USP dissolution apparatus buffered at a pH of 6.8.

The dosage form of the current invention was placed in a USP dissolution apparatus buffered at a pH of 6.8. The amount of hydrocodone bitartrate released as a percentage of total hydrocodone bitartrate contained in the dosage form was quantified at timepoints of 0, 1, 2, 4, 6, 8, and 12 hours. These data are shown in FIG. 7.

Based on these data, the average release rate from 0-1, 1-2, 2-4, 4-6, 6-8, and 8-12 hours was calculated. These data are shown in FIG. 8.

Figure 8:
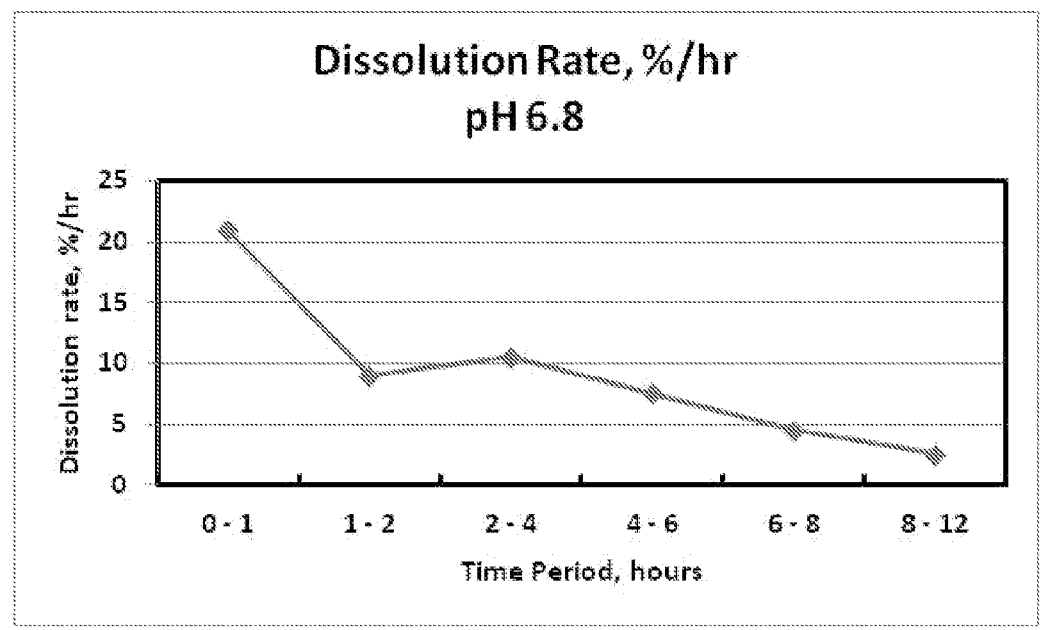
FIG. 8 is a plot of the data from FIG. 7 displayed as an average rate of release over each time period.

FIG. 8 clearly shows the immediate release and sustained release components of the formulation. Approximately 21% of the hydrocodone was rapidly released in the first hour. The remainder of the hydrocodone was released at a relatively constant rate of approximately 5%-10% per hour during the period from 1 to 8 hours, and at an average rate of approximately 2.5% per hour from 8 through 12 hours.

Example 8

A clinical study was performed to determine the influence of hepatic impairment on the pharmacokinetics and relative bio availability of hydrocodone and its metabolites following the administration under fasted conditions of HC-ER containing 20 mg of hydrocodone bitartrate. The dosage forms were prepared as described in example 6 and shown to demonstrate the dissolution profile as described in example 7.

This study employed a single-dose, parallel-group design. Subjects were admitted to the clinic on day 1 for qualification procedures and on day 1 received a single dose of HC-ER (20 mg). Doses of HC-ER were administered following an overnight fast (8 hours), and subjects did not eat for at least 4 hours after dose administration. All doses were administered with 240 mL of ambient temperature water. Study participants were housed in the clinical research facility throughout the treatment period, beginning on the evening prior to administration of the test medication and extending through collection of all blood and urine samples.

Thirty (30) subjects were enrolled in the study. Ten (10) healthy control subjects were matched to 20 hepatically-impaired subjects for age (±10 years), and body mass index (BMI) (±10% of BMI) with some consideration for race and gender (see FIG. 2). The hepatically-impaired subjects had a diagnosis of chronic (more than 6 months), stable (no acute episodes of illness within the previous 2 months due to deterioration of hepatic function) hepatic insufficiency with features of cirrhosis due to any etiology. Ten (10) hepatically-impaired subjects were enrolled into each of two Child-Pugh classifications based on their hepatic impairment: mild and moderate. The majority of subjects enrolled were male (22 of 30, 73.3%) and white (26 of 30, 86.7%). The mean age of all subjects was 56.5 years. Mean weight of subjects was 84.01 kg, mean height was 170.73 cm, and mean BMI was 28.90 kg/m2. Thirteen (13) of the 30 subjects (43.3%) were Hispanic or Latino, while 17 of the 30 subjects (56.7%) were non-Hispanic or non-Latino.

Blood samples for pharmacokinetic (PK) assessment were obtained from all subjects just prior to dose administration (time zero) and at 1, 2, 3, 4, 5, 6, 7, 8, 10, 12, 18, 24, 30, 36, 48, 60, and 72 hours after dose administration. The concentration of hydrocodone was measured in the blood samples using a validated assay method.

Overall, hydrocodone concentrations increased with decreasing hepatic function. Although the differences in mean exposures ($AUC_{0-inf}$ and $C_{max}$) were statistically significant, the magnitude of the differences was modest ($AUC_{0-inf}$ 10% higher and $C_{max}$ 8% higher in subjects with mild hepatic impairment and $AUC_{0-inf}$ 26% higher and $C_{max}$ 10% higher in subjects with moderate impairment (see FIG. 1). Furthermore, there was considerable overlap in the hydrocodone AUC (see FIG. 4) and $C_{max}$ (see FIG. 5) across cohorts, indicating that the increase in hydrocodone exposure secondary to hepatic impairment, while statistically significant, was relatively mild and not clinically significant.

FIG. 6 compares the plasma hydrocodone concentration curves across the three cohorts. As can be seen from the curves, the pharmacokinetics, while statistically significantly different, are very similar. These differences would not be considered large enough to require dosage adjustment for patients with hepatic impairment. In fact, the considerable overlap in the distributions of PK exposure amongst impairment cohorts is such that any a priori dose adjustment could potentially result in patients receiving inadequate hydrocodone doses.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating pain in a patient having mild or moderate hepatic impairment, the method comprising:
administering to the patient having mild or moderate hepatic impairment an oral dosage unit having hydrocodone bitartrate as the only active ingredient, wherein the dosage unit comprises an extended release formulation of hydrocodone bitartrate, wherein the dose is not adjusted for the patient having mild or moderate hepatic impairment and wherein the dosage unit provides a plasma half-life of hydrocodone of about 8 hours in patients without hepatic impairment.

2. The method of claim 1, wherein the dosage unit provides a plasma half-life of hydrocodone of about 9 hours in patients with mild hepatic impairment.

3. The method of claim 1, wherein the dosage unit provides a plasma half-life of hydrocodone of about 10 hours in patients with moderate hepatic impairment.

4. The method of claim 1, wherein the dosage unit comprises about 20 mg of hydrocodone bitartrate.

5. A method of treating pain in a patient having mild hepatic impairment, the method comprising:
administering to the patient having mild hepatic impairment an oral dosage unit having about 20 mg of hydrocodone bitartrate as the only active ingredient, wherein the dosage unit comprises an extended release formulation of hydrocodone bitartrate.

6. A method of treating pain in a patient having moderate hepatic impairment, the method comprising:
administering to the patient having moderate hepatic impairment an oral dosage unit having about 20 mg of hydrocodone bitartrate as the only active ingredient, wherein the dosage unit comprises an extended release formulation of hydrocodone bitartrate.

7. A method of treating pain in a patient having mild or moderate hepatic impairment, the method comprising:

administering to the patient having mild or moderate hepatic impairment an oral dosage unit having hydrocodone bitartrate as the only active ingredient, wherein the dosage unit comprises a first formulation of hydrocodone bitartrate and a second formulation of hydrocodone bitartrate, and wherein the dose is not adjusted relative to a patient without hepatic impairment.

8. The method of claim 7, wherein the dosage unit provides a release profile of hydrocodone such that:
  (1) the mean hydrocodone $AUC_{0-inf}$ per 20 mg of hydrocodone bitartrate dosed to subjects not suffering from renal or hepatic impairment is in the range of about 317 ng*h/mL to about 466 ng*h/mL; and
  (2) the mean hydrocodone $AUC_{0-inf}$ per 20 mg of hydrocodone bitartrate dosed to subjects suffering from moderate hepatic impairment is in the range of about 352 ng*h/mL to about 666 ng*h/mL.

9. The method of claim 7, wherein the first formulation comprises an immediate release component and the second formulation comprises a sustained release component.

10. The method of claim 9, wherein the immediate release component comprises a first population of particles and the sustained release component comprises a second population of particles.

11. The method of claim 7, wherein the first formulation comprises 15 to 25 percent by weight of the total hydrocodone in the oral dosage unit and the second formulation comprises 75 to 85 percent by weight of the total hydrocodone in the oral dosage unit.

12. The method of claim 7, wherein the dosage unit comprises a multiparticulate modified release composition.

13. The method of claim 12, wherein the dosage unit comprises a capsule containing the multiparticulate modified release composition.

14. The method of claim 13, wherein the multiparticulate modified release composition comprises a first population of beads containing 15 to 25% by weight of the total hydrocodone in the oral dosage unit as an immediate release population, and a second population of beads containing 75 to 85 percent by weight of the total hydrocodone in the oral dosage unit as a sustained release population.

15. The method of claim 14, wherein the multiparticulate modified release composition comprises a third population of beads which are different from beads in the first and second populations of beads.

16. The method of claim 14, wherein the second population of beads comprises a polymer coating comprising one or more of cellulose acetate phthalate, cellulose acetate trimaletate, hydroxy propyl methylcellulose phthalate, polyvinyl acetate phthalate, ammonio methacrylate copolymers, polyacrylic acid, polyacrylate and methacrylate copolymers, polyvinyl acetaldiethylamino acetate, hydroxypropyl methylcellulose acetate succinate and shellac.

17. The method of claim 16, wherein the polymer coating comprises ammonio methacrylate copolymers.

18. The method of claim 17, wherein the first population of beads and the second population of beads comprise sugar spheres as an inert core.

19. The method of claim 18, wherein the dosage unit provides a release profile of hydrocodone such that:
  (1) the mean hydrocodone $AUC_{0-inf}$ per 20 mg of hydrocodone bitartrate dosed to subjects not suffering from renal or hepatic impairment is in the range of about 317 ng*h/mL to about 466 ng*h/mL; and
  (2) the mean hydrocodone $AUC_{0-inf}$ per 20 mg of hydrocodone bitartrate dosed to subjects suffering from moderate hepatic impairment is in the range of about 352 ng*h/mL to about 666 ng*h/mL.

20. The method of claim 19, wherein the dosage unit provides a release profile of hydrocodone such that the mean hydrocodone $AUC_{0-inf}$ per 20 mg of hydrocodone bitartrate subjects suffering from mild hepatic impairment is in the range of about 316 ng*h/mL to about 563 ng*h/mL.

* * * * *